United States Patent [19]

King et al.

[11] Patent Number: 5,708,174

[45] Date of Patent: Jan. 13, 1998

[54] HETEROCYCLIC-ESTERS OR -AMIDES USED AS 5-HT$_4$ RECEPTOR ANTAGONISTS

[75] Inventors: Francis David King; Laramie Mary Gaster, both of Bishop's Stortford; Graham Francis Joiner, Brentwood; Keith Raymond Mulholland, Harlow; Shirley Katherine Rahman, Bishop's Stortford, all of England

[73] Assignee: SmithKline Beecham p.l.c., Brentford, England

[21] Appl. No.: 416,773

[22] PCT Filed: Oct. 8, 1993

[86] PCT No.: PCT/EP93/02775

§ 371 Date: Apr. 11, 1995

§ 102(e) Date: Apr. 11, 1995

[87] PCT Pub. No.: WO94/08994

PCT Pub. Date: Apr. 28, 1994

[30] Foreign Application Priority Data

| Mar. 12, 1992 | [GB] | United Kingdom | 9305138 |
| Mar. 12, 1992 | [GB] | United Kingdom | 9305155 |
| Oct. 13, 1992 | [GB] | United Kingdom | 9221442 |
| Oct. 13, 1992 | [GB] | United Kingdom | 9221443 |

[51] Int. Cl.$^6$ ............ C07D 215/227; C07D 215/06; A61K 31/47
[52] U.S. Cl. .......... 546/157; 546/168; 546/169; 546/166; 546/170; 546/138; 514/312; 514/306; 514/211; 514/311; 514/314; 540/593
[58] Field of Search .............. 546/157, 168, 546/169, 166, 170, 138; 514/312, 306, 211, 311, 314; 540/593

[56] References Cited

U.S. PATENT DOCUMENTS 5,620,992 4/1997 King ........................ 514/321

FOREIGN PATENT DOCUMENTS

| 0 108 986 | 5/1984 | European Pat. Off. |
| 0 231 139 | 8/1987 | European Pat. Off. |
| 0 328 200 | 8/1989 | European Pat. Off. |
| 0 445 862 | 9/1991 | European Pat. Off. |
| 0 499 995 | 8/1992 | European Pat. Off. |
| WO93/02677 | 2/1993 | WIPO. |
| WO93/05040 | 3/1993 | WIPO. |
| 93/16072 | 8/1993 | WIPO. |

OTHER PUBLICATIONS

King, F.D. and Sanger, G.J; "5-HT$_3$ Receptor Antagonists"; Drugs of the Future vol. 14, No. 9, 1989; pp. 875–889.

Evans S.M., Galdes, A., Gall, M.; "Molecular Modeling of 5-HT$_3$ Receptor Ligands"; Pharmacology Biochemistry & Behavior, vol. 40, 1991; pp. 1033–1040.

*Primary Examiner*—C. Warren Ivy
*Assistant Examiner*—D. Margaret M. Mach
*Attorney, Agent, or Firm*—Soma G. Simon; Charles M. Kinzig; Edward T. Lentz

[57] ABSTRACT

Compounds of formula (I), wherein formula I consists of formulae (I-1) to (I-4), which are defined in the specification, and pharmaceutically acceptable salts thereof, and the use of a compound of formula I or a pharmaceutically acceptable salt thereof, and their use as pharmaceuticals in the treatment of gastrointestinal disorders, cardiovascular disorders and CNS disorder.

11 Claims, No Drawings

HETEROCYCLIC-ESTERS OR -AMIDES USED AS 5-HT₄ RECEPTOR ANTAGONISTS

This invention relates to novel compounds having pharmacological activity, to a process for their preparation and to their use as pharmaceuticals.

European Journal of Pharmacology 146 (1988), 187–188, and Naunyn-Schmiedeberg's Arch. Pharmacol. (1989) 340:403–410, describe a non classical 5-hydroxytryptamine receptor, now designated the 5-HT$_4$ receptor, and that ICS 205-930, which is also a 5-HT$_3$ receptor antagonist, acts as an antagonist at this receptor. WO 91/16045 (SmithKline and French Laboratories Limited) describes the use of cardiac 5-HT$_4$ receptor antagonists in the treatment of atrial arrhythmias and stroke.

EP-A-501322 (Glaxo Group Limited) describes indole derivatives having 5-HT$_4$ antagonist activity.

WO 93/02677, WO 93/03725, WO 93/05038, WO 93/05040 and PCT/GB93/00506 (SmithKline Beecham plc) describe compounds having 5-HT$_4$ receptor antagonist activity.

It has now been discovered that certain novel compounds also have 5-HT$_4$ receptor antagonist properties.

When used herein, 'treatment' includes prophylaxis as appropriate.

Accordingly, the present invention provides compounds of formula (I), wherein formula (I) consists of formulae (I-1) to (I-4), and pharmaceutically acceptable salts thereof, and the use of a compound of formula (I) or a pharmaceutically acceptable salt thereof:

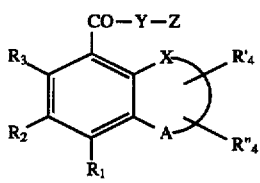
(I-1)

wherein
X is O or S;
A is CH=CH—CH$_2$, CO—(CH$_2$)$_2$ or CH(OR$_x$)—(CH$_2$)$_2$ wherein R$_x$ is hydrogen or C$_{1-6}$ alkyl;
R$_1$ is hydrogen, amino, halo, C$_{1-6}$ alkyl, hydroxy or C$_{1-6}$ alkoxy;
R$_2$ is hydrogen, halo, C$_{1-6}$ alkyl, C$_{1-6}$ alkoxy, nitro, amino or C$_{1-6}$ alkylthio;
R$_3$ is hydrogen, halo, C$_{1-6}$ alkyl, C$_{1-6}$ alkoxy or amino;
R$_4$' and R$_4$" are independently hydrogen or C$_{1-6}$ alkyl;

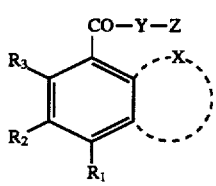
(I-2)

wherein
X is —N=CH—CH=CH— or —NR$_4$—(CH$_2$)$_3$—;
R$_1$ is hydrogen, amino, halo, C$_{1-6}$ alkyl, hydroxy or C$_{1-6}$ alkoxy;
R$_2$ is hydrogen, halo, C$_{1-6}$ alkyl, C$_{1-6}$ alkoxy, nitro, amino or C$_{1-6}$ alkylthio;
R$_3$ is hydrogen, halo, C$_{1-6}$ alkyl, C$_{1-6}$ alkoxy or amino;
R$_4$ is hydrogen or C$_{1-6}$ alkyl;

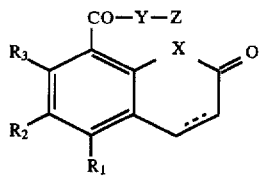
(I-3)

wherein
X is O or NR$_4$, where R$_4$ is hydrogen or C$_{1-6}$ alkyl;
--- represents a single or double bond;
R$_1$ is hydrogen, amino, halo, C$_{1-6}$ alkyl, hydroxy or C$_{1-6}$ alkoxy;
R$_2$ is hydrogen, halo, C$_{1-6}$ alkyl, C$_{1-6}$ alkoxy, nitro, amino or C$_{1-6}$ alkylthio;
R$_3$ is hydrogen, halo, C$_{1-6}$ alkyl, C$_{1-6}$ alkoxy or amino;

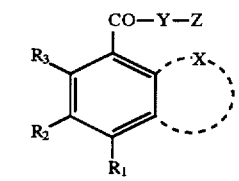
(I-4)

wherein
X is —NR$_4$—CH$_2$CH—CH—;
R$_1$ is hydrogen, amino, halo, C$_{1-6}$ alkyl, hydroxy or C$_{1-6}$ alkoxy;
R$_2$ is hydrogen, halo, C$_{1-6}$ alkyl, C$_{1-6}$ alkoxy, nitro, amino or C$_{1-6}$ alkylthio;
R$_3$ is hydrogen, halo, C$_{1-6}$ alkyl, C$_{1-6}$ alkoxy or amino;
R$_4$ is hydrogen or C$_{1-6}$ alkyl;
In formulae (I-1) to (I-4) inclusive:
Y is O or NH;
Z is of sub-formula (a), (b) or (c):

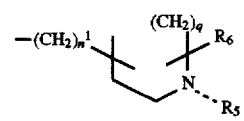
(a)

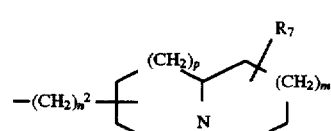
(b)

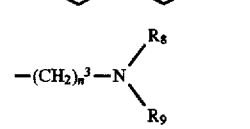
(c)

wherein
n$^1$ is 0, 1, 2, 3 or 4; n$^2$ is 0, 1, 2, 3 or 4; n$^3$ is 2, 3, 4 or 5;
q is 0, 1, 2 or 3; p is 0, 1 or 2; m is 0, 1 or 2;
R$_5$ is hydrogen, C$_{1-12}$ alkyl, aralkyl or R$_5$ is (CH$_2$)$_z$—R$_{10}$ wherein z is 2 or 3 and R$_{10}$ is selected from cyano, hydroxyl, C$_{1-6}$ alkoxy, phenoxy, C(O)C$_{1-6}$ alkyl, COC$_6$H$_5$, —CONR$_{11}$R$_{12}$, NR$_{11}$COR$_{12}$, SO$_2$NR$_{11}$R$_{12}$ or NR$_{11}$SO$_2$R$_{12}$ wherein R$_{11}$ and R$_{12}$ are hydrogen or C$_{1-6}$ alkyl; and
R$_6$, R$_7$ and R$_8$ are independently hydrogen or C$_{1-6}$ alkyl; and
R$_9$ is hydrogen or C$_{1-10}$ alkyl;
or a compound of formula (I) wherein the CO—Y linkage is replaced by a heterocyclic bioisostere;

in the manufacture of a medicament having 5-HT$_4$ receptor antagonist activity.

Examples of alkyl or alkyl containing groups include $C_1$, $C_2$, $C_3$, $C_4$, $C_5$, $C_6$, $C_7$, $C_8$, $C_9$, $C_{10}$, $C_{11}$ or $C_{12}$ branched, straight chained or cyclic alkyl, as appropriate. $C_{1-4}$ alkyl groups include methyl, ethyl, n- and iso-propyl, n-, iso-, sec- and tert-butyl. Cyclic alkyl includes cyclopropyl, cyclobutyl, cyclopentyl, cyclohexyl, cycloheptyl and cyclooctyl.

Aryl includes phenyl and naphthyl optionally substituted by one or more substituents selected from halo, $C_{1-6}$ alkyl and $C_{1-6}$ alkoxy.

Halo includes fluoro, chloro, bromo and iodo.

In formula (I-1):

$R_1$ is preferably hydrogen or amino.

$R_2$ is preferably hydrogen or halo.

$R_3$ is preferably hydrogen or halo.

$R_4'$ and $R_5''$ are often hydrogen.

In formula (I-2):

$R_1$ is preferably hydrogen or amino.

$R_2$ is preferably hydrogen or halo.

$R_3$ is preferably hydrogen or halo.

$R_4$ is often hydrogen.

In formula (I-3):

$R_1$ is preferably hydrogen or amino.

$R_2$ is preferably hydrogen or halo.

$R_3$ is preferably hydrogen or halo.

$R_4$ is preferably hydrogen or methyl.

In formula (I-4):

$R_1$ is preferably hydrogen or amino.

$R_2$ is preferably hydrogen or halo.

$R_3$ is preferably hydrogen or halo.

$R_4$ is often hydrogen.

A suitable bioisostere for the amide or ester linkage containing Y in formula (I), is of formula (d):

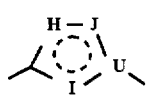

(d)

wherein the dotted circle represents one or two double bonds in any position in the 5-membered ring; H, J and I independently represent oxygen, sulphur, nitrogen or carbon, provided that at least one of H, J and I is other than carbon; U represents nitrogen or carbon.

Suitable examples of (d) are as described for X, Y and Z in EP-A-328200 (Merck Sharp & Dohme Ltd.), such as an oxadiazole moiety.

Y is preferably O or NH.

When Z is of sub-formula (a), $n^1$ is preferably 2, 3 or 4 when the azacycle is attached at the nitrogen atom and $n^1$ is preferably 1 when the azacycle is attached at a carbon atom, such as the 4-position when q is 2.

When Z is of sub-formula (b), $n^2$ is preferably such that the number of carbon atoms between the ester or amide linkage is from 2 to 4 carbon atoms.

Suitable values for p and m include p=m=1; p=0, m=1, p=1, m=2, p=2, m=1.

When Z is of sub-formula (c), $n^3$ is preferably 2, 3 or 4.

$R_8$ and $R_9$ are preferably both alkyl, especially one of $R_8$ and $R_9$ is $C_4$ or larger alkyl.

Specific values of Z of particular interest are as follows:

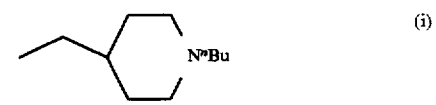

(i)

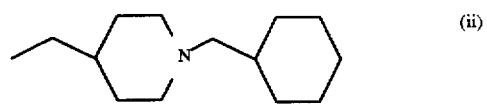

(ii)

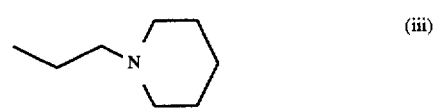

(iii)

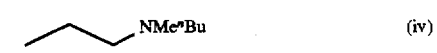

(iv)

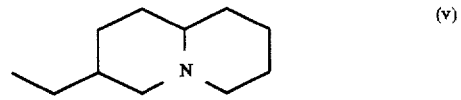

(v)

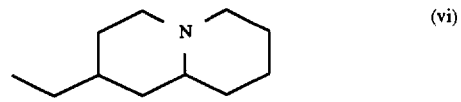

(vi)

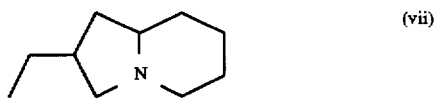

(vii)

The invention also provides novel compounds within formula (I) with side chains (i), (ii), (iii), (iv), (v), (vi) or (vii). In a further aspect, the piperidine ring in (i), (ii) or (iii) may be replaced by pyrrolidinyl or azetidinyl, and/or the N-substituent in (i) or (ii) may be replaced by $C_3$ or larger alkyl or optionally substituted benzyl.

In an alternative aspect, the N-substituent in formula (i) or (ii) may be replaced by $(CH_2)_n R^4$ as defined in formula (I) and in relation to the specific examples of EP-A-501322.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

Examples of pharmaceutically acceptable salts include quaternary derivatives of the compounds of formula (I) such as the compounds quaternised by compounds $R_x$-T wherein $R_x$ is $C_{1-6}$ alkyl, phenyl-$C_{1-6}$ alkyl or $C_{5-7}$ cycloalkyl, and T is a radical corresponding to an anion of an acid. Suitable examples of $R_x$ include methyl, ethyl and n- and iso-propyl; and benzyl and phenethyl. Suitable examples of T include halide such as chloride, bromide and iodide.

Examples of pharmaceutically acceptable salts also include internal salts such as N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

The compounds of formula (I) wherein CO—Y is an ester or amide linkage are prepared by conventional coupling of the Z moiety with the appropriate acid. Suitable methods are as described in GB 2125398A (Sandoz Limited), GB 1593146A, EP-A-36269, EP-A-289170 and WO 92/05174 (Beecham Group p.l.c.). When CO—Y is replaced by a heterocyclic bioisostere, suitable methods are described in EP-A-328200 (Merck Sharp & Dohme Limited). Reference is also made to EP-A-501322 (Glaxo Group Limited).

The invention also comprises a process for preparing the novel compounds of formula (I) which comprises reacting an appropriate acid derivative with an appropriate alcohol or amine. A process comprises reacting an acid derivative wherein the aromatic substituents are as required in the end compound of formula (I), or substituents convertible thereto, with an alcohol or amine containing Z or a group convertible thereto, and thereafter if necessary, converting the benzoic acid substituents and/or Z, and optionally forming a pharmaceutically acceptable salt.

Suitable examples of conversions in the aromatic substituents include chlorination of hydrogen to chloro, reduction of nitro to amino, dehydrohalogenation such as debromination. Any elaboration is, however, usually carried out prior to ester or amide coupling.

Suitable examples of conversions in the Z containing moiety include conventional modifications of the N-substituent by substitution and/or deprotection or, in the case of a 2-, 3- or 4- substituted piperidinyl desired end compound, reduction of an appropriate pyridyl derivative.

The compounds of the present invention are $5\text{-HT}_4$ receptor antagonists and it is thus believed may generally be used in the treatment or prophylaxis of gastrointestinal disorders, cardiovascular disorders and CNS disorders.

They are of potential interest in the treatment of irritable bowel syndrome (IBS), in particular the diarrhoea aspects of IBS, i.e., these compounds block the ability of 5-HT to stimulate gut motility via activation of enteric neurones. In animal models of IBS, this can be conveniently measured as a reduction of the rate of defaecation. They are also of potential use in the treatment of urinary incontinence which is often associated with IBS.

They may also be of potential use in other gastrointestinal disorders, such as those associated with upper gut motility, and as antiemetics. In particular, they are of potential use in the treatment of the nausea and gastric symptoms of gastro-oesophageal reflux disease and dyspepsia. Antiemetic activity is determined in known animal models of cytotoxic-agent/radiation induced emesis.

Specific cardiac $5\text{-HT}_4$ receptor antagonists which prevent atrial fibrillation and other atrial arrhythmias associated with 5-HT, would also be expected to reduce occurrence of stroke (see A. J. Kaumann 1990, Naunyn-Schmiedeberg's Arch. Pharmacol. 342, 619–622, for appropriate animal test method).

Anxiolytic activity is likely to be effected via the hippocampus (Dumuis et al 1988, Mol Pharmacol., 34, 880–887). Activity can be demonstrated in standard animal models, the social interaction test and the X-maze test.

Migraine sufferers often undergo situations of anxiety and emotional stress that precede the appearance of headache (Sachs, 1985, Migraine, Pan Books, London). It has also been observed that during and within 48 hours of a migraine attack, cyclic AMP levels are considerably increased in the cerebrospinal fluid (Welch et al, 1976, Headache 16, 160–167). It is believed that a migraine, including the prodomal phase and the associated increased levels of cyclic AMP are related to stimulation of $5\text{-HT}_4$ receptors, and hence that administration of a $5\text{-HT}_4$ antagonist is of potential benefit in relieving a migraine attack.

Other CNS disorders of interest include schizophrenia, Parkinson's disease and Huntingdon's chorea.

The invention also provides a phhrmaceutical composition comprising a compound of formula (I), or a pharmaceutically acceptable salt thereof, and a pharmaceutically acceptable carrier.

Such compositions are prepared by admixture and are usually adapted for enteral such as oral, nasal or rectal, or parenteral administration, and as such may be in the form of tablets, capsules, oral liquid preparations, powders, granules, lozenges, reconstitutable powders, nasal sprays, suppositories, injectable and infusable solutions or suspensions. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantifies of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of irritable bowel syndrome, dyspepsia, atrial arrhythmias and stroke, anxiety and/or migraine in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.05 to 1000 mg for example 0.5 to 500 mg, of the compound of the invention. Unit doses may be administered once or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated within the aforementioned dosage ranges.

The invention also provides a compound of formula (I) or a pharmaceutically acceptable salt thereof for use as an active therapeutic substance, in particular for use in the treatment of irritable bowel syndrome, gastro-oesophageal reflux disease, dyspepsia, atrial arrhythmias and stroke, anxiety and/or migraine.

The following Examples illustrates the preparation of compounds of formula (I), and the following Descriptions relate to the preparation of intermediates. The compounds of formula (I-1) and intermediates are prepared in Examples and Descriptions 1-1, 2-1 etc, the compounds of formula (I-2) are prepared in Examples and Descriptions 1-2, 2-2 etc and similarly for the compounds of formulae (I-3) to (I-4).

It will be appreciated that any compound prepared wherein Y is O may be provided as the corresponding compound wherein Y is NH.

A preferred compound corresponds to any of the compounds prepared in the Examples, but wherein there is an amino substituent in the 4-position and a chloro substituent in the 5-position of the benzoic acid nucleus depicted in formulae (I-1) to (I-4) inclusive.

EXAMPLE 1-1

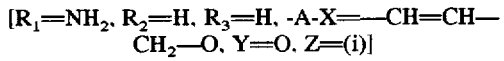

(1-Butyl4-piperidinylmethyl)-5-amino-[2H]-1-benzopyran-8-carboxylate

To a solution of 5-amino-[2H]-1-benzopyran-8-carboxylic acid (200 mg, 1.05 mmol) in acetonitrile (7 ml) was added N,N'-carbonyldiimidazole (204 mg, 1.26 mmol). Stirring was continued at ambient temperature for 1 h. The solvent was concentrated in vacuo to afford the crude imidazolide.

Methyllithium (1.5M in diethylether, 0.74 ml) was added dropwise to a cooled (0° C.) solution of 1-butyl-4-piperidinylmethanol (179 mg, 1.05 mmol) in dry THF (5 ml) under a nitrogen atmosphere. Stirring was continued at room temperature for 10 minutes. A solution of the imidazolide in dry THF (10 ml) was added and stirring continued overnight. Water was added and the solvent concentrated in vacuo. The residue was partitioned between chloroform and water. The organic phase was dried ($Na_2SO_4$), filtered and concentrated. The residue was chromatographed on silica using chloroform and methanol as eluant to afford the pure ester (45 mg, 14%) as a solid. Treatment with ethanol HCl and triturnation of the resultant gum with diethyl ether gave the title compound as a solid.

$^1$H NMR (250 MHz, $CDCl_3$)(free base) δ: 7.52(d, 1H), 6.35(d, 1H), 6.18 (d, 1H), 5.82–5.68 (m, 1H), 4.7 (s, 2H), 4.1—3.9 (m, 4H), 2.89 (d, 2H), 2.4–2.2 (m, 2H), 1.98 (t, 2H), 1.75 (d, 3H), 1.6–1.34 (m, 4H), 1.33–1.15 (m, 2H), 0.85 (t, 3H).

EXAMPLE 2-1

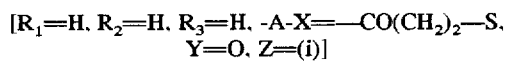

(1-Butyl-4-piperidinyl-methyl)thiochroman-4-one-8-carboxylate

This was prepared according to the general method outlined in Example 1-1. Thus thiochroman-4-one-8-carboxylic acid (0.500 g, 2.40 mmol) was converted to the title compound (0.258 g, 30%) which was subsequently convened to its hydrochloride salt. m.pt 165°–166° C.

$^1$H NMR (250 MHz, $CDCl_3$)(free base) δ: 8.35 (dd, 1H), 8.12 (dd, 1H), 7.21 (t, 1H), 4.20 (d, 2H), 3.15 (m, 2H), 2.98 (m, 4H), 2.35 (t, 2H), 1.98 (t, 2H), 1.68 (m, 2H), 1.60–1.20 (m, 7H), 0.90 (t, 3H).

EXAMPLE 3-1

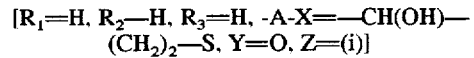

(1-Butyl-4-piperidinylmethyl)thiochroman-4-ol-8-carboxylate (1-Butylpiperidin-4-ylmethyl)thiochroman-4-one-8-carboxylate (0.064 g, 0.177 mmol)(Example 2-1) was dissolved in ethanol (5 ml) and treated with sodium borohydride (0.007 g, 0.186 mmol) with stirring. After 3 h, the reaction mixture was evaporated under reduced pressure and the residue partitioned between $CH_2Cl_2$ and water. The aqueous layer was then extracted with $CH_2Cl_2$ and the combined organic extracts were dried ($Na_2SO_4$) and evaporated under reduced pressure to give the title compound as a pale yellow oil which was dried in vacuo (0.060 g, 93%) and subsequently converted to the oxalate salt. m.pt 147°–148° C.

$^1$H NMR (270 MHz, $CDCl_3$)(free base) δ: 7.92 (d, 1H), 7.50 (d, 1H), 7.10 (t, 1H), 4.82 (s, 1H), 4.17 (d, 1H), 3.20 (dt, 1H), 2.88 (m, 3H), 2.30 (t, 3H), 2.15 (m, 7H), 1.55–1.20 (m, 6H), 0.90 (t, 3H).

EXAMPLE 4-1

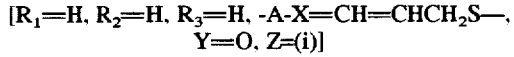

(1-Butyl-4-piperidinylmethyl)-2H-thiochromene-8-carboxylate

This was prepared according to the general method described in Example 1. Thus 2H-thiochromene-8-carboxylic acid (0.184 g, 0.948 mmol) was converted to the title compound (0.205 g, 63%) and subsequently transformed to its oxalate salt m.pt 150°–155° C. (decomp).

$^1$H NMR (200 MHz, $CDCl_3$)(free base), δ 7.80 (dd, 1H), 7.20 (dd, 1H), 7.10 (t, 1H), 6.52 (d, 1H), 6.00 (m, 1H), 4.20 (d, 2H), 3.35 (dd, 2H), 3.00 (m, 2H), 2.38 (t, 2H), 2.00 (t, 2H), 1.83 (m, 2H), 1.60–1.20 (m, 7H), 0.92 (t, 3H)

DESCRIPTION 1-1 (INTERMEDIATE FOR EXAMPLE 1-1)

a) Methyl(4-acetylamino-2-propargyloxy)benzoate

A solution of methyl-4-acetylamino-2-hydroxybenzoate (prepared as described in EP-A-234872) (5 g) in a mixture of dry tetrahydrofuran (100 ml) and dry dimethylformamide (150 ml) was treated with 1 equivalent of sodium hydride (0.72 g of an 80% dispersion in oil). After stirring for 1 hour under nitrogen, 2.5 equivalents of propargylbromide (5.33 ml) were added, and the mixture was heated under reflux for three days. The solvents were evaporated under reduced pressure and the residue partitioned between 10% sodium hydroxide and ethyl acetate. The organic phase was dried over $Na_2SO_4$ and evaporated under reduced pressure to give a red oil which, after trituration with 60°–80° petrol-ether gave the title compound as a light tan powder (4.95 g, 84%)
$^1$H NMR 200 MHz ($CDCl_3$) δ: 7.9(brs, 1H), 7.81(d, 1H), 7.68(s, 1H), 7.05(d, 1H), 4.78(d,2H), 3.86(s,3H), 2.54(m, 1H), 2.2(s,3H)

b) Methyl-(5-acetamido-[2H]-1-benzopyran)-8-carboxylate

A solution of methyl-(4-acetamido-2-propargyloxy)benzoate (6.38g) in 1,2-dichlorobenzene (65 ml) was heated under reflux under nitrogen for 60 hours. The solvent was evaporated under reduced pressure and the residue purified on a silica column, eluting with methanol/chloroform, to give the title compound as a tan solid (3.47 g, 54%)
$^1$H NMR 200 MHz ($CDCl_3$) δ: 7.79(brs, 1H), 7.64(d, 1H), 7.3(d, 1H), 6.46(d, 1H), 5.85(m, 1H), 4.75(brs,2H), 3.85(s, 3H), 2.20(s,3H)

c) 5-Amino-[2H]-1-benzopyran-8-carboxylic acid

A solution of methyl-(5-acetamido-[2H]- 1-benzopyran)-8-carboxylate (1.21 g, 5.93 mmol) in 10% aq NaOH (20 ml), ethanol 910 ml) and water (10ml) was heated to reflux for 20 hours.

The ethanol was evaporated under reduced pressure and the residue was treated with concentrated hydrochloric acid and the resulting precipitate filtered off and washed with water, to give the title compound (605 mg, 65%)
$^1$H NMR (250 MHz, $CD_3SOCD_3$) δ: 7.4 (d, 1H), 6.7 (d, 1H), 6.42 (d, 1H), 6.35–5.5 (m, 3H), 4.67 (s, 2H).

DESCRIPTION 2-1 (INTERMEDIATE FOR EXAMPLE 2-1)

Thiochroman-4-one-8-carboxylic acid

β(2-Carbomethoxythiophenoxy)propionic acid (6.00 g, 0.025 mol) (I. W. Still and M. J. Thomas J. Org. Chem 1968, 2733) was added slowly to ice cooled conc. sulphuric acid (75 ml) with stirring. After 21 h, the reaction mixture was poured into ice water and then made alkaline using solid sodium hydrogen carbonate. The resultant suspension was then extracted with $CH_2Cl_2$(3x). The combined organic layers were then dried ($Na_2SO_4$), and evaporated under reduced pressure to give an orange oil which was dried in vacuo and crystallised on standing to give methylthiochroman-4-one-8-carboxylate (2.40 g, 43%)
$^1$H NMR (200 MHz, $CDCl_3$), δ:: 8.32 (dd, 1H), 8.12 (dd, 1H), 7.24 (t, 1H), 3.92 (s, 3H), 3.15 (m, 2H), 3.00 (m, 2H).

The basic aqueous layer was faltered through kieselguhr and acidified to pH1 using c. HCl. The resultant precipitate was then faltered off and dried in vacuo to give the title compound as an off white solid (1.01 g, 20%).
$^1$H NMR (200 MHz, $CD_3SOCD_3$) δ: 8.20 (dd, 1H), 8.08 (dd, 1H) 7.30 (t, 1H), 3.20 (t, 2H), 2.90 (t, 2H).

DESCRIPTION 2-1 (INTERMEDIATE FOR EXAMPLE 4-1)

a) Methylthiochroman-4-ol-8-carboxylate

Methylthiochroman-4-one-8-carboxylate (0.500 g, 2.25mmol) was dissolved with stirring in ethanol (20 ml) and treated with sodium borohydride (0.085 g, 2.25 mmol). After 1 h, the reaction mixture was evaporated under reduced pressure and the residue partitioned between ethyl acetate and water. The aqueous layer was then extracted with ethyl acetate (1 x) and the combined organic layers were dried ($Na_2SO_4$) and evaporated under reduced pressure to give a yellow oil, which was purified by silica-gel chromatography (1:1 Pentane:EtOAc as eluant) to give the title compound as a colourless oil (0.499 g, 99%)
$^1$H NMR (200 MHz, $CDCl_3$) δ: 7.95 (dd, 1H), 7.55 (dd, 1H), 7.12 (t, 1H), 4.87 (m, 1H), 3.92 (s, 3H) 3.23 (m, 1H), 2.88 (m, 1H), 2.37 (m, 1H), 2.08 (m, 1H), 1.92 (d, 1H).

b) Methyl-2H-thiochromene-8-carboxylate

Methyl thiochroman-4-ol-8-carboxylate (0.337 g, 1.50 mmol) was dissolved in toluene (25 ml) and was treated with p-toluenesulphonic acid (0.028 g, 0.15 mmol). The mixture was then heated to reflux with stirring. After 2 h, the reaction mixture was allowed to cool and was washed with sodium hydrogen carbonate solution. The aqueous layer was then extracted with EtOAc (1x), and the combined organic layers were dried ($Na_2SO_4$) and evaporated under reduced pressure to give a pale yellow oil which was purified by silica-gel chromatography (pentane: $Et_2O$ 2:1 as eluant) to give the title compound as a pale yellow oil (0.270 g, 87%)
$^1$H NMR (200 MHz, $CDCl_3$, δ: 7.80 (dd, 1H), 7.20 (dd, 1H), 7.10 (t, 1H), 6.52 (d, 1H), 6.02 (m, 1H), 3.92 (s, 3H), 3.48 (dd, 1H).

c) 2H-Thiochromene-8-carboxylic acid

Methyl-2H-thiochromene-8-carboxylate (0.300 g, 1.46 mmol) was dissolved in ethanol (5 ml) and treated with 10% sodium hydroxide solution (10 ml). The mixture was then heated to reflux with stirring. After 5 h, the reaction mixture was allowed to cool The ethanol present was then removed by evaporation under reduced pressure. The aqueous residue was then washed with $CH_2Cl_2$ (2x) before being acidified to pH1 using 5M HCl. The resultant pale yellow precipitate was then filtered off and dried in vacuo to give the title compound (0.195 g, 69%) as a pale yellow solid.
$^1$H NMR (250 MHz, $CD_3SOCD_3$) δ: 13.10 (brs, 1H) 7.68 (d, 1H) 7.30 (d, 1H) 7.12 (t, 1H), 6.58 (d, 1H), 6.02 (m, 1H), 3.30 (dd, 2H).

EXAMPLE 1-2

[$R_1$, $R_2$, $R_3$=H, X=—N—CH—CH=CH, Y=O, Z=(i)]

(1-Butyl-4-piperidinylmethyl)quinolinyl-8-carboxylate hydrochloride

To a solution of quinoline-8-carboxylic acid (250mg) in dichloromethane (10 ml) was added oxalyl chloride (122 ml) and 2 drops of N,N'-dimethylformamide. Stirring was continued at room temperature for 2 h. The solvent was concentrated in vacuo to afford crude acid chloride as a solid.

MeLi (933 ml, 1.5M in diethyl ether) was added to a cooled (0° C) solution of 1-butyl-4-piperidinemethanol (240 mg) in dry THF (10 ml). Stirring was continued at room temperature for 15 min. A solution of the crude acid chloride in dry THF (10 ml) was added and stirring continued overnight. Water (1 ml) was added and the solvent concentrated in vacuo. The residue was partitioned between chloroform and water. The organic phase was dried ($Na_2SO_4$), filtered and concentrated in vacuo. Chromatography on silica gave pure ester (170 mg) which was treated with ethereal HCl to afford title compound.

¹H NMR 250 MHz (CDCl₃) Free base
δ: 9.05(dd, 1H), 8.19(d, 1H), 8.05(d, 1H), 7.97(d, 1H), 7.58(t, 1H), 7.46(dd, 1H), 4.34(d,2H), 3.03(d,2H), 2.39(t, 2H), 1.82—2.08(m,5H), 1.43—1.62(m,4H), 1.21—1.39(m, 2H), 0.94(t,3H)

EXAMPLE 2-2

[R₁, R₂, R₃=H, X=—NG—(CH₂)₃—, Y=O, X= (i)]

(1-Butyl-4-piperidinylmethyl)-1,2,3,4-tetrahydroquinoline-8-carboxylate hydrochloride The title compound was prepared from 1,2,3,4-tetrahydroquinoline-8-carboxylic acid by the method described for Example 1-2.

¹H NMR 250 MHz (CD₃OD) δ:7.78(d,1H),7.11(d,1H),6.50 (t,1H),3.41— 3.57(m,2H),2.85(t,2H),1.89—2.07(m,2H)

DESCRIPTION 1-2 (INTERMEDIATE FOR EXAMPLE 2-2)

1,2,3,4-Tetrahydroquinoline-8-carboxylic acid

A solution of quinoline-8-carboxylic acid (85 mg) in ethanol (15 ml) was hydrogenated over PtO₂ (250 mg) at 50 psi and room temperature for 2 hours. The catalyst was removed by filtration through keiselguhr and the filtrate concentrated in vacuo to afford the title compound (80 mg).

¹H NMR 250 MHz (CD₃OD)
δ: 7.78(d,1H),7.11(d,1H),6.50(t,1H),3.41—3.57(m,2H), 2.85(t,2H),1.89—2.07(m,2H)

The following compounds are prepared from the corresponding acid and lithium (1-butyl-4-piperidinyl) methoxide via the imidazolide.

EXAMPLE 1-3

[R₁, R₂, R₃=H, X=NH, --- is double bond, Y=O, Z=(i)]

8-(1-Butyl-4-piperidinylmethyl)-1,2-dihydro-2-oxoquinolinecarboxylate

EXAMPLE 2-3

[R₁, R₂, R₃=H, X=NH, --- is single bond, Y=O, Z=(i)]

8-(1-Butyl-4-piperidinylmethyl)- 1,2,3,4-tetrahydro-2-oxoquinolinecarboxylate

EXAMPLE 1-4

[R₁, R₂, R₃=H, X=—NCH₃—CH₂CH=CH—, Y=O, Z=(i)]

8-(1-Butyl-4-piperidinylmethyl)- 1,2-dihydro-1-methylquinolinecarboxylate

5-HT₄ RECEPTOR ANTAGONIST ACTIVITY

1) Guinea pig colon

Male guinea-pigs, weighing 250–400 g are used. Longitudinal muscle-myenteric plexus preparations, approximately 3 cm long, are obtained from the distal colon region. These are suspended under a 0.5 g load in isolated tissue baths containing Krebs solution bubbled with 5% $CO_2$ in $O_2$ and maintained at 37° C. In all experiments, the Krebs solution also contains methiothepin $10^{-7}$M and granisetron $10^{-6}$M to block effects at 5-HT₁, 5-HT₂ and 5-HT₃ receptors.

After construction of a simple concentration-response curve with 5-HT, using 30s contact times and a 15 min dosing cycle, a concentration of 5-HT is selected so as to obtain a contraction of the muscle approximately 40–70% maximum( $10^{-9}$M approx). The tissue is then alternately dosed every 15 min with this concentration of 5-HT and then with an approximately equi-effective concentration of the nicotine receptor stimulant, dimethylphenylpiperazinium (DMPP). After obtaining consistent responses to both 5-HT and DMPP, increasing concentrations of a putative 5-HT₄ receptor antagonist are then added to the bathing solution. The effects of this compound are then determined as a percentage reduction of the contractions evoked by 5-HT or by DMPP. From this data, pIC₅₀ values are determined, being defined as the -log concentration of antagonist which reduces the contraction by 50%. A compound which reduces the response to 5-HT but not to DMPP is believed to act as a 5-HT₄ receptor antagonist.

The compounds generally had a pIC₅₀ of at least 6, the compound of Example 1-2 having particularly good activity.

We claim:

1. Compounds of formula (I), wherein formula (I) consists of formulae (I-2) to (I-4), and pharmaceutically acceptable salts thereof:

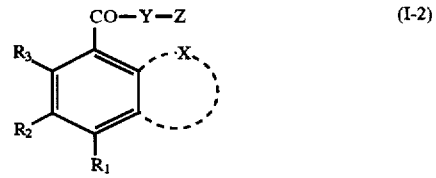
(I-2)

wherein X is —N=CH—CH=CH— or —NR₄—(CH₂)₃—;

R₁ is hydrogen, amino, halo, $C_{1-6}$ alkyl, hydroxy or $C_{1-6}$ alkoxy;

R₂ is hydrogen, halo, $C_{1-6}$ alkyl, $C_{1-6}$ alkoxy, nitro, amino or $C_{1-6}$ alkylthio;

R₃ is hydrogen, halo, $C_{1-6}$ alkyl, $C_{1-6}$ alkoxy or amino;

R₄ is hydrogen or $C_{1-6}$ alkyl;

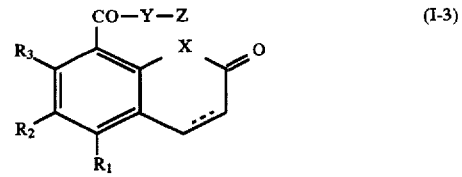
(I-3)

wherein X is NR₄, where R₄ is hydrogen or $C_{1-6}$ alkyl;

--- represents a single or double bond;

R₁ is hydrogen, amino, halo, $C_{1-6}$ alkyl, hydroxy or $C_{1-6}$ alkoxy;

R₂ is hydrogen, halo, $C_{1-6}$ alkyl, $C_{1-6}$ alkoxy, nitro, amino or $C_{1-6}$ alkylthio;

$R_3$ is hydrogen, halo, $C_{1-6}$ alkyl, $C_{1-6}$ alkoxy or amino;

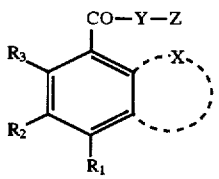
(I-4)

wherein X is $-NR_4-CH_2CH=CH-$;
$R_1$ is hydrogen, amino, halo, $C_{1-6}$ alkyl, hydroxy or $C_{1-6}$ alkoxy;
$R_2$ is hydrogen, halo, $C_{1-6}$ alkyl, $C_{1-6}$ alkoxy, nitro, amino or $C_{1-6}$ alkylthio;
$R_3$ is hydrogen, halo, $C_{1-6}$ alkyl, $C_{1-6}$ alkoxy or amino;
$R_4$ is hydrogen or $C_{1-6}$ alkyl;
wherein in formulae (I-2) to (I-4) inclusive:
Y is O or NH;
Z is of sub-formula (a), (b) or (c):

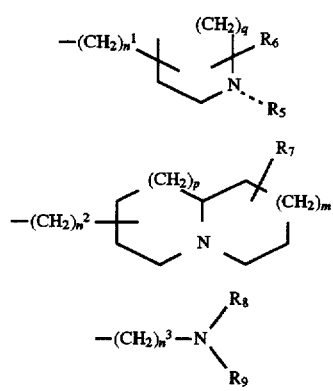

wherein $n^1$ is 0, 1, 2, 3 or 4; $n^2$ is 0, 1, 2, 3 or 4; $n^3$ is 2, 3, 4 or 5;
q is 0, 1, 2 or 3; p is 0, 1 or 2; m is 0, 1 or 2;
$R_5$ is hydrogen, $C_{1-12}$ alkyl, aralkyl or $R_5$ is $(CH_2)_z-R_{10}$ wherein z is 2 or 3 and $R_{10}$ is selected from cyano, hydroxyl, $C_{1-6}$ alkoxy, phenoxy, $C(O)C_{1-6}$ alkyl, $COC_6H_5$, $-CONR_{11}R_{12}$, $NR_{11}COR_{12}$, $SO_2NR_{11}R_{12}$ or $NR_{11}SO_2R_{12}$ wherein $R_{11}$ and $R_{12}$ are hydrogen or $C_{1-6}$ alkyl; and
$R_6$, $R_7$ and $R_8$ are independently hydrogen or $C_{1-6}$ alkyl; and
$R_9$ is hydrogen or $C_{1-10}$ alkyl;
or a compound of formula (I) wherein the CO—Y linkage is replaced by a heterocyclic bioisostere of formula (d):

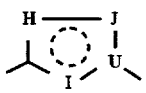
(d)

wherein the dotted circle represents one or two double bonds in any position in the 5 membered ring;

H, J and I independently represent oxygen, sulphur, nitrogen or carbon, provided that at least one of H, J and I is other than carbon; and U represents nitrogen or carbon.

2. A compound according to claim 1 wherein:

in formula (I-2): $R_1$ is hydrogen or amino, $R_2$ is hydrogen or halo, $R_3$ is hydrogen or halo, $R_4$ is hydrogen;

in formula (I-3): $R_1$ is hydrogen or amino, $R_2$ is hydrogen or halo, $R_3$ is hydrogen or halo, $R_4$ is hydrogen or methyl;

in formula (I-4): $R_1$ is hydrogen or amino, $R_2$ is hydrogen or halo, $R_3$ is hydrogen or halo, $R_4$ is hydrogen.

3. A compound according to claim 1 wherein Z is of sub-formula (a) and $(CH_2)_n1$ is attached at a carbon atom of the azacycle.

4. A compound according to claim 3 wherein Z is N-substituted 4-piperidylmethyl.

5. A compound according to claim 4 wherein Z is 4-piperidylmethyl and $R^5$ is $C_2$ or greater alkyl, or optionally substituted benzyl.

6. A compound selected from the group consisting of: (1-butyl-4-piperidinylmethyl)quinolinyl-8-carboxylate, and (1-butyl-4-piperidinylmethyl)-1, 2, 3, 4-tetrahydroquinoline-8-carboxylate, and pharmaceutically acceptable salts thereof.

7. A compound selected from the group consisting of:

8-(1-butyl-4-piperidinylmethyl)-1, 2-dihydro-2-oxoquinolinecarboxylate, and 8-(1-butyl-4-piperidinylmethyl)-1, 2, 3, 4-tetrahydro-2-oxoquinolinecarboxylate, and pharmaceutically acceptable salts thereof.

8. A compound selected from:

8-(1-Butyl-4-piperidinylmethyl)-1, 2-dihydro-1-methylquinolinecarboxylate, and pharmaceutically acceptable salts thereof.

9. A pharmaceutical composition comprising a compound according to any one of claims 1 to 8, and a pharmaceutically acceptable carrier.

10. A compound according to claim 1 wherein Y-Z is

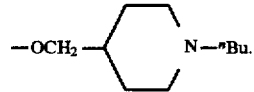

11. A method of treatment of gastrointestinal disorders, cardiovascular disorders and CNS disorders which comprises administration of a compound according to claim 1.

* * * * *